(12) United States Patent
Togashi et al.

(10) Patent No.: US 10,874,473 B2
(45) Date of Patent: Dec. 29, 2020

(54) CONTAINER

(71) Applicant: DAIKYO SEIKO LTD., Sano (JP)

(72) Inventors: Hiroshi Togashi, Sano (JP); Hideaki Kawamura, Sano (JP)

(73) Assignee: DAIKYO SEIKO LTD., Sano (JP)

(*) Notice: Subject to any disclaimer, the term of this patent is extended or adjusted under 35 U.S.C. 154(b) by 0 days.

(21) Appl. No.: 16/095,812

(22) PCT Filed: Apr. 28, 2017

(86) PCT No.: PCT/JP2017/016902
§ 371 (c)(1),
(2) Date: Oct. 23, 2018

(87) PCT Pub. No.: WO2017/188427
PCT Pub. Date: Nov. 2, 2017

(65) Prior Publication Data
US 2019/0125473 A1 May 2, 2019

(30) Foreign Application Priority Data

Apr. 28, 2016 (JP) .................................. 2016-090235

(51) Int. Cl.
*A61M 5/00* (2006.01)
*A61B 50/39* (2016.01)
(Continued)

(52) U.S. Cl.
CPC ............... *A61B 50/39* (2016.02); *A61M 5/00* (2013.01); *A61M 5/001* (2013.01); *A61M 5/002* (2013.01);
(Continued)

(58) Field of Classification Search
USPC ................................................. 206/364, 370
See application file for complete search history.

(56) References Cited

U.S. PATENT DOCUMENTS 3,681,092 A * 8/1972 Titchenal et al. ........ A23B 4/16
426/412
4,055,672 A * 10/1977 Hirsch .................... B65D 81/24
426/127
(Continued)

FOREIGN PATENT DOCUMENTS

CN 103562088 A 2/2014
CN 104743259 A 7/2015
(Continued)

OTHER PUBLICATIONS

Europe Patent Office, "Search Report for European Patent Application No. 17789708.9," dated Sep. 13, 2019.
(Continued)

*Primary Examiner* — Jacob K Ackun
(74) *Attorney, Agent, or Firm* — Manabu Kanesaka

(57) ABSTRACT

To provide a container for a medical device, which enables easy removal of wrapping, thereby significantly reducing the labor for unpacking at the delivery destination such as a pharmaceutical company or a medical institution. Furthermore, the provided container for the medical device enables easy removal of wrapping even during an automated process in a filling machine for medical solutions, for example. In this container for a medical device, a holder holding at least one medical device is placed inside a container body having an opening at the top, and the opening is sealed with a gas-impermeable film. When sterilizing the exterior of the container using a sterilization gas, the sterilization gas does not permeate into the container due to the gas-impermeable film, so the medical device and the holder thereof placed inside the container are never exposed to the gas.

2 Claims, 14 Drawing Sheets

(51) Int. Cl.
  *B65D 77/20* (2006.01)
  *B65D 25/20* (2006.01)
  *B65D 81/20* (2006.01)
(52) U.S. Cl.
  CPC ............ *A61M 5/008* (2013.01); *B65D 25/20* (2013.01); *B65D 77/20* (2013.01); *B65D 81/20* (2013.01); *A61M 2205/7518* (2013.01)

(56) References Cited

U.S. PATENT DOCUMENTS

| | | | |
|---|---|---|---|
| 4,142,633 A * | 3/1979 | Raghavachari | A61M 5/008 141/27 |
| 4,479,762 A * | 10/1984 | Bilstad | A61M 1/3496 206/364 |
| 5,779,050 A * | 7/1998 | Kocher | B32B 27/08 206/497 |
| 6,012,595 A * | 1/2000 | Thilly | A61M 5/008 211/60.1 |
| 6,164,044 A * | 12/2000 | Porfano | B65B 55/10 422/28 |
| 6,585,942 B1 * | 7/2003 | Bussell | A61L 2/26 206/349 |
| 7,296,678 B2 * | 11/2007 | Raynal-Olive | A61L 2/208 206/370 |
| 8,118,167 B2 * | 2/2012 | Togashi | A61M 5/008 206/519 |
| 8,151,987 B2 * | 4/2012 | Kimball | A61F 13/00063 206/440 |
| 8,623,289 B2 * | 1/2014 | Cesa | A61L 2/26 206/363 |
| 9,598,195 B2 | 3/2017 | Deutschle et al. | |
| 2004/0022674 A1 | 2/2004 | Thurk et al. | |
| 2004/0118852 A1 * | 6/2004 | Barmore | B65D 77/2044 220/359.2 |
| 2006/0073244 A1 * | 4/2006 | Brackenridge | A23B 4/16 426/129 |
| 2008/0183140 A1 | 7/2008 | Paproski et al. | |
| 2009/0095647 A1 * | 4/2009 | Togashi | A61M 5/008 206/438 |
| 2009/0100802 A1 | 4/2009 | Bush et al. | |
| 2010/0012537 A1 * | 1/2010 | Farrar | A61M 5/008 206/364 |
| 2010/0012546 A1 * | 1/2010 | Togashi | A61M 5/008 206/534.1 |
| 2010/0270392 A1 * | 10/2010 | Trent | A01M 1/2077 239/55 |
| 2010/0307956 A1 * | 12/2010 | Lepot | B65D 25/103 206/571 |
| 2011/0192756 A1 * | 8/2011 | Hill | A61M 5/008 206/515 |
| 2013/0048531 A1 | 2/2013 | Nicoletti | |
| 2014/0013718 A1 * | 1/2014 | Maasarani | A61M 5/002 53/492 |
| 2014/0027326 A1 | 1/2014 | Peruzzo | |
| 2014/0102927 A1 * | 4/2014 | Liversidge | B01L 9/54 206/364 |
| 2014/0190861 A1 * | 7/2014 | Carrel | B65D 71/0096 206/518 |
| 2014/0353190 A1 * | 12/2014 | Okihara | B65D 1/22 206/370 |
| 2015/0013276 A1 * | 1/2015 | Okajima | B65B 3/003 53/471 |
| 2015/0182686 A1 | 7/2015 | Okihara | |
| 2018/0134423 A1 * | 5/2018 | Narvekar | A61M 5/008 |
| 2019/0070357 A1 * | 3/2019 | Evans | A61M 5/008 |

FOREIGN PATENT DOCUMENTS

| | | |
|---|---|---|
| JP | 2005-335782 A | 12/2005 |
| JP | 2006-16005 A | 1/2006 |
| JP | 2006-36227 A | 2/2006 |
| JP | 2013-525218 A | 6/2013 |
| JP | 3184488 U | 6/2013 |
| JP | 5412275 B2 | 2/2014 |
| WO | 2014/109011 A1 | 7/2014 |

OTHER PUBLICATIONS

PCT/ISA/210, "International Search Report for International Application No. PCT/JP2017/016902," dated Jun. 20, 2017.
China Patent Office, "Office Action for Chinese Patent Application No. 201780026096.0," dated Jul. 22, 2019.

* cited by examiner

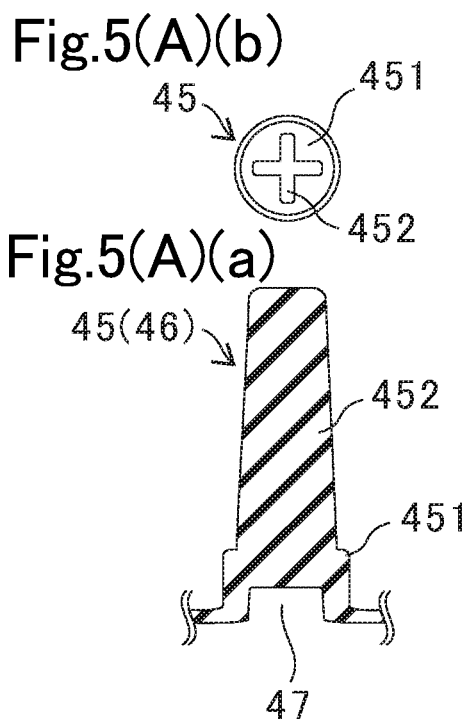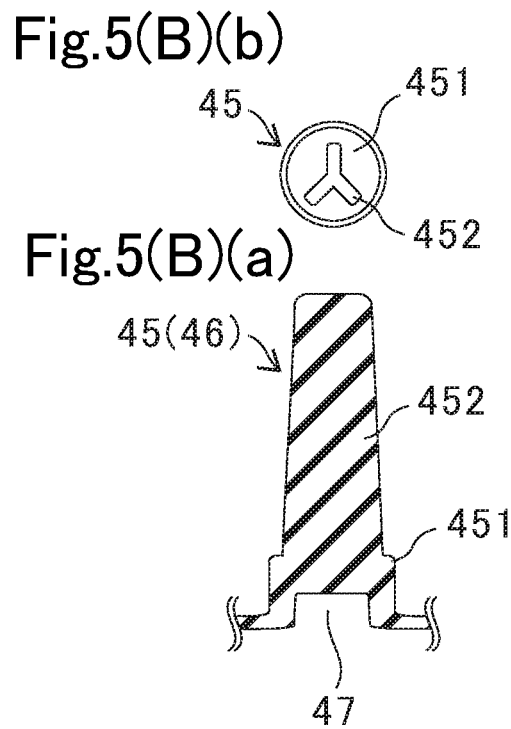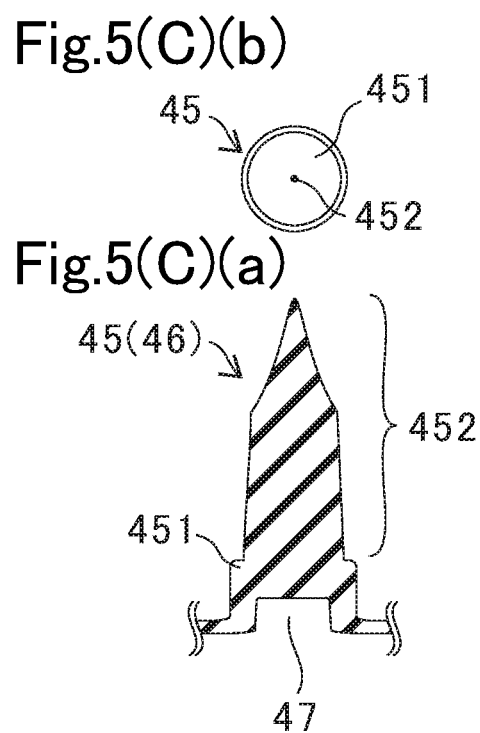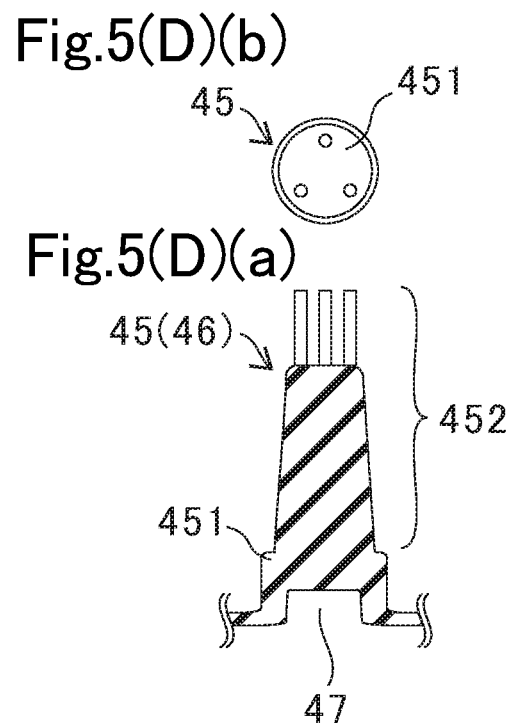

CONTAINER

RELATED APPLICATIONS

The present application is National Phase of International Application No. PCT/JP2017/016902 filed Apr. 28, 2017, and claims priority from Japanese Application No. 2016-090235, filed Apr. 28, 2016, the disclosure of which is hereby incorporated by reference herein in its entirety.

TECHNICAL FIELD

The present invention relates to a container for a medical device which houses a holder for holding a medical device, which can be sterilized and transferred in a sterilized condition.

BACKGROUND ART

Because a medical device is required to be sterilized, the medical device is stored in a packaging body for sterilization and a sterilization process is conducted by steam, electron beam, radial ray, plasma, ethylene oxide gas, etc. Such a packaging body for sterilization is constituted to be packaged by a gas permeable base material, e.g., paper or no-woven cloth which passes gas like steam or ethylene oxide gas and blocks bacteria, and an article to be sterilized is enclosed in the packaging body and a sterilization process is applied.

For example, US2004/0022674A1 (Patent Document 1) proposed a container for a medical device which can be sterilized or transferred in a sterilized condition.

PRIOR ART LITERATURES

Patent Literatures

Patent Literature 1: American Unexamined Patent Application Publication No. US2004/0022674A1
Patent Literature 2: Japanese Registered Patent Publication No. 5412275

DISCLOSURE OF INVENTION

Problems to be Resolved by the Invention

The container for a medical device shown in Patent Document 1 is constituted by forming an opening at the top portion, mounting a holder in the container for holding a medical device, holding the medical device in the holder, sealing the opening by a cover which is gas permeable and bacteria non-permeable and wrap-packaging the entire sealed container.

The container for a medical device shown in Patent Document 1 is delivered to a pharmaceutical company or a medical institution after sterilization, however, in general, it takes a lot of trouble because it requires operations for removing the wrap package under a sterilization environment and then removing the cover which seals the opening portion of the container in order to utilize the medial device at the delivered site. Especially, when a medical agent is filled in the medical device using a filling machine by an automated process, it was not easy to remove the wrap package in such a process.

Therefore, the task of the present invention is to provide a container for a medical device which can significantly reduce labor hour for removing the seal at a delivered site, e.g., a pharmaceutical company or a medical institution by making the removal of the package easier. Furthermore, the task of the present invention is to provide a container for a medical device which enables an easy removal of the package even during an automated process in a filling machine for filling a medical agent in the medical device.

The inventor of the present invention studied hard to resolve the above-mentioned problem. Consequently, the following invention was made.

(1) A container having an opening portion at its top portion and housing a holder for holding at least one medical device, wherein the opening portion is sealed by a gas non-permeable film.

(2) A container described in (1), wherein the container, the medial device, holder and the gas non-permeable film are sterilized.

(3) A container described in (1) or (2), wherein the gas non-permeable comprises a sterilizable film which can be sterilized by gas, steam or radial ray and a gas non-permeable film, and the sterilizable film is positioned on the side contacting the container.

(4) A container described in either one of (1) through (3), wherein the space between the sterilizable film and the gas non-permeable film is sterilized.

Means for Solving the Problems

In a container for a medical device according the present invention, it is possible to significantly reduce the labor hour for removing a seal at a delivered site like a pharmaceutical company or a medical institution by removing a package easily.

Furthermore, it is possible to remove a package easily during an automated process in a filling machine for filling a medical agent in the medical device.

Additionally, in a container for a medical device according the present invention, it becomes unnecessary to sterilize the medical device again at a delivered site of the medical device which is housed in the container.

By this arrangement, it is possible to efficiently fill a medical agent during an automated filling process for filling the medical agent in a medical device like a vial, and additionally it is possible to easily perform an automatic capping of a rubber plug to a medical device like a vial after the medical agent filling.

Furthermore, during a sterilization of the outer side of the container by a sterilization gas, the medical device and its holder in the container are not exposed to gas because the sterilization gas does not go into the container with the aid of the gas non-permeable film.

It is also possible to deliver the container to a user in a condition where the outer side of the container is sterilized when the entire container is covered by a gas non-permeable film.

BRIEF DESCRIPTION OF DRAWINGS

FIGS. 5(A)(a), 5(A)(b), 5(B)(a), 5(B)(b), 5(C)(a), 5(C)(b), 5(D)(a), and 5(D)(b) show examples of side support rods which are mounted on the holder shown in FIGS. 4(A) and 4(B); in each drawing, FIGS. 5(A)(a), 5(B)(a), 5(C)(a), and 5(D)(a) show a side view and FIGS. 5(A)(b), 5(B)(b), 5(C)(b), and 5(D)(b) show a bottom view.

FIG. 6(*a*) shows a side view and FIG. 6(*b*) shows a bottom view.

A MODE FOR IMPLEMENTING THE INVENTION

Embodiment 1

Figure 1:
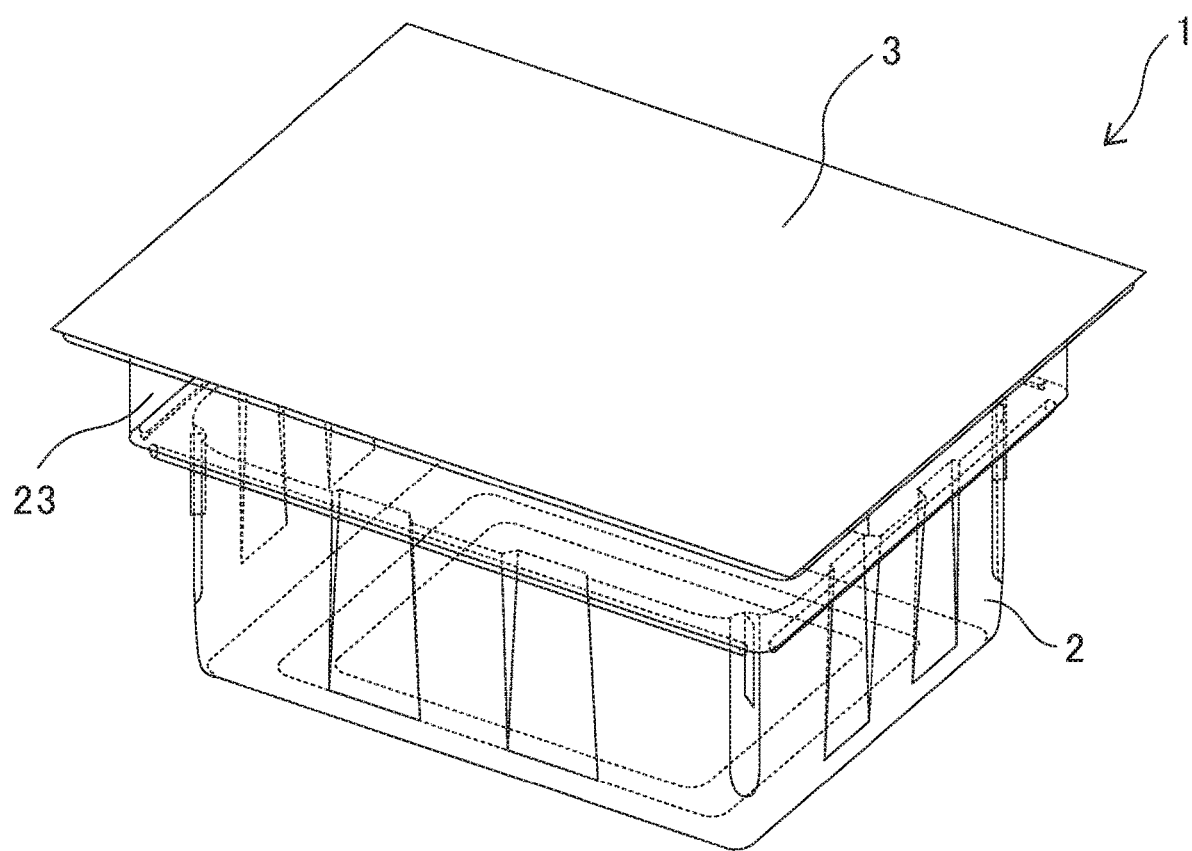
FIG. 1 shows a perspective view of the embodiment 1 of the entire container for a medical device according to the present invention.

FIGS. 1 through 7 show the embodiment 1 of a medical device container 1 according to the present invention. As shown in FIGS. 1 through 3(C) and 7, the medical device container 1 according to the embodiment 1 comprises a container body 2 having an opening at the top portion, a medical device holder 4 which is housed in the container body 2 and a gas non-permeable film 3 for sealing the opening portion at the top portion of the container body 2.

Figure 2A:
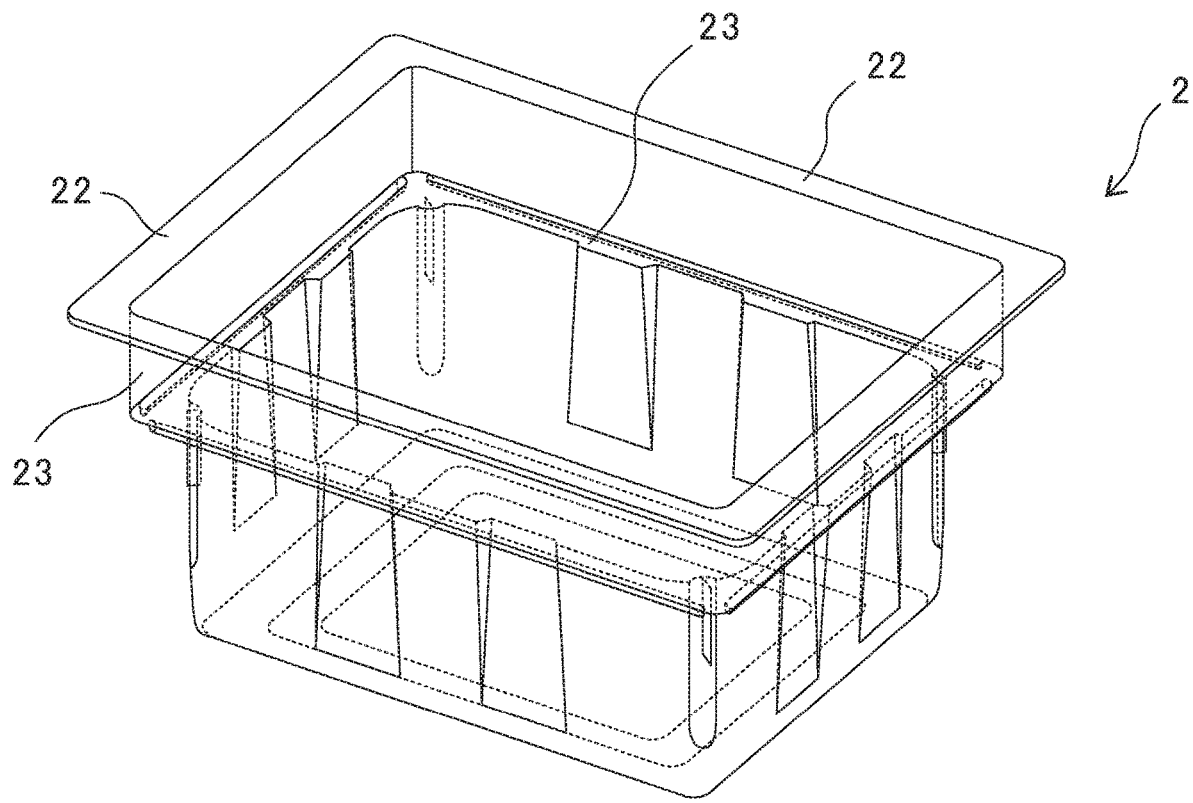
FIG. 2(A) shows a perspective view of the container body for a medical device shown in FIG. 1.
Figure 2B:
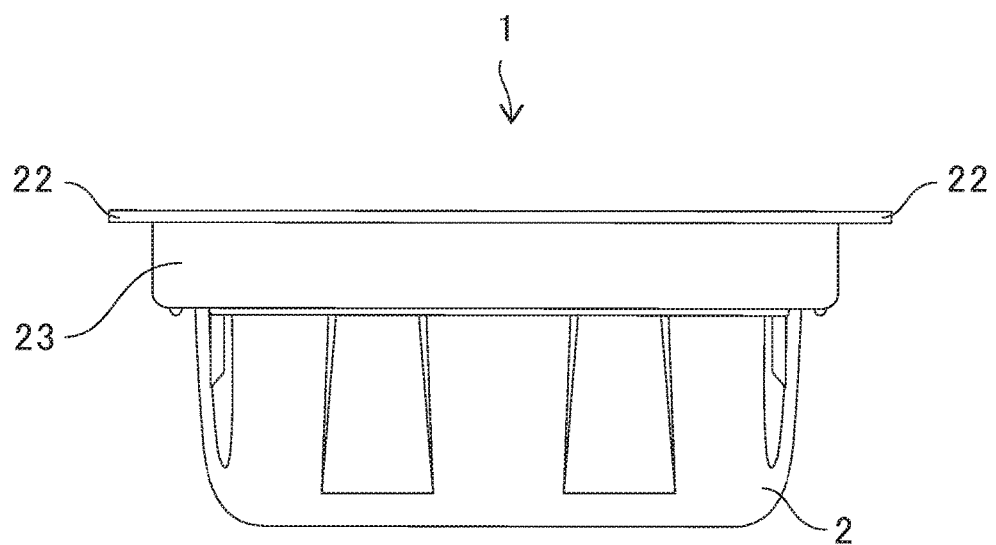
FIG. 2(B) shows a front view of the container body for a medical device shown in FIG. 1.

As shown in FIGS. 1 and 2(A) and 2(B), the container body 2 is formed in a basket (box) shape having a nearly rectangular planer shape, and comprises a circular flange portion 22 which is formed at the opening portion of the top portion to extend circularly and outward and an uneven portion 23 which is formed circularly at a position which is lower than the circular flange portion 22 by a predetermined length toward the bottom. The planer shape of the container body 2 may be a polygonal shape, a circular shape or an oval shape, other than the nearly rectangular shape shown in the drawing. The container body 2 is formed by synthetic resin, metal or various composites of these materials.

The gas non-permeable film 3 seals the circular flange portion 22 of the container body 2 such that they are peelable by heat welding and the like, and then seals the opening portion at the top portion of the container body 2. It is preferable that the gas non-permeable film 3 comprises a gas non-permeable film which blocks gas, steam, bacteria, etc., and a sterilizable film which is positioned and stacked on the side contacting the container body 2. It is also possible to seal the opening portion by sealing the circular flange portion 22 of the container body 2 with the sterilizable film by heat welding and the like such that they are peelable, covering the entire container by the gas non-permeable film 3 and then packaging the container body 2 by vacuuming. The sterilizable film passes gaseous matter for sterilization like gas, steam or the like, but does not pass bacteria, and is formed by filaments of high density polyethirene or other polymers, for example.

It is possible to use "Tyvek" (Registered Trademark) made by DuPont as a sterilizable film and a film made of polyvinylidene chloride, high density polyethylene, polyethylene terephthalate or the like as the gas non-permeable film.

Figure 3A:
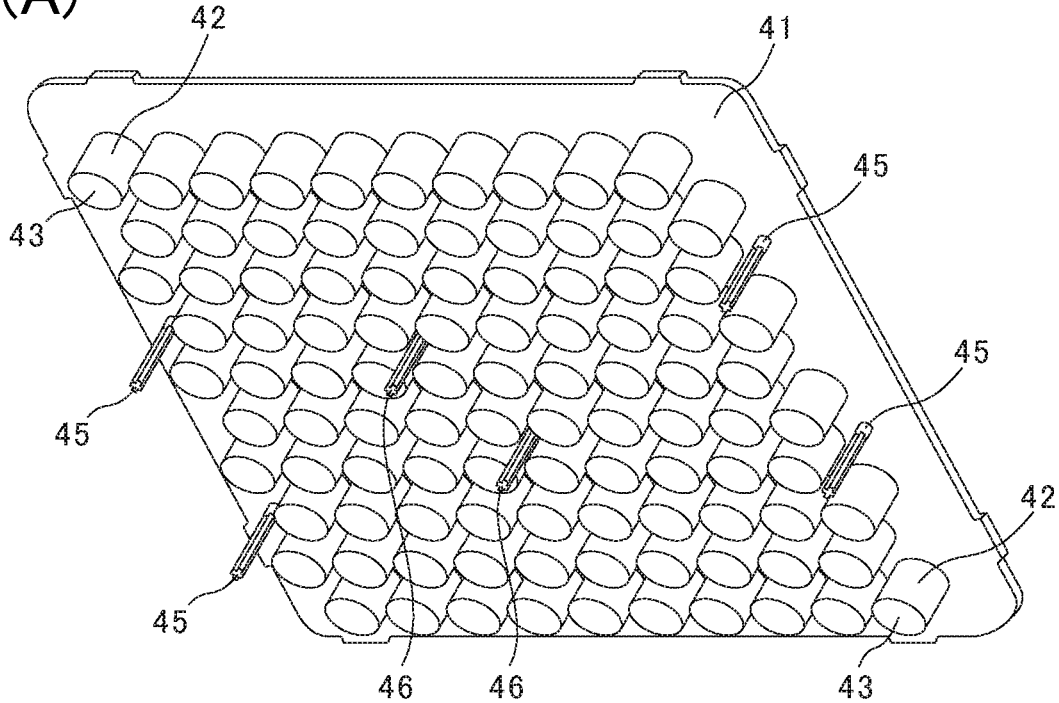
FIG. 3 (A) shows a perspective view of a holder which is housed in the container for a medical device shown in FIG.
FIG. 3(B) shows a plan view of the holder shown in FIG. 3(A)
FIG. 3(C) shows a front view of the holder shown in FIG. 3(A).
Figure 3B:
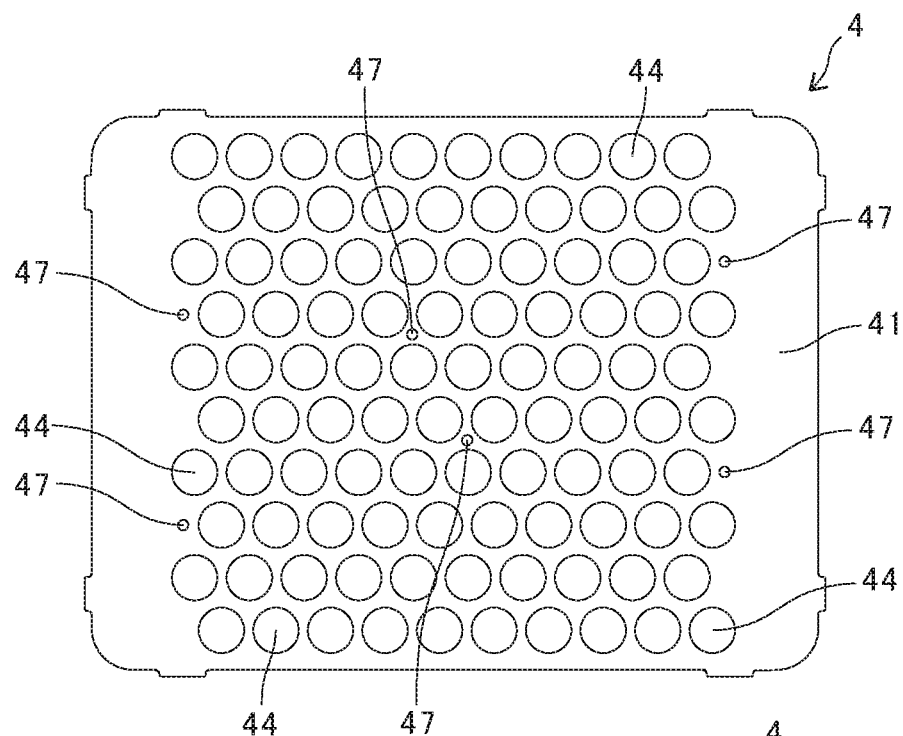
Figure 7:
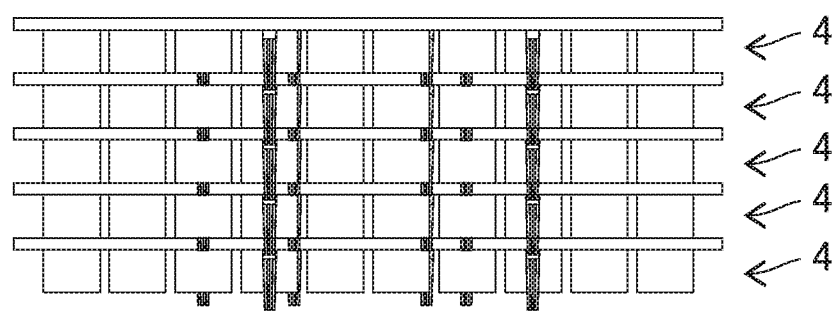
FIG. 7 shows a side view of a condition where the holders shown in FIGS. 3(A), 3(B), and 3(C) are stacked and housed in the container shown in FIG. 1.

The medical device holder 4 is placed alone inside the container body 2 or plural medical device holders 4 are stacked and placed in the container body 2 as shown in FIG. 7 to house the medical device holder 4 in the container body 2. As shown in FIGS. 3(A) and 3(B), the holder 4 comprises a plate-like basal plate portion 41 and plural tubular portions 42 protruding downward from the basal plate portion 41. The shape of the basal plate portion 41 may be nearly rectangular as shown in the drawing, circular, oval or polygonal. The number of tubular portion 42 and the distance between neighboring tubular portions 42 are not limited specifically, however it is preferable to place the neighboring tubular portions 42 at nearly equal intervals. By this arrangement, it is possible not only to place a large number of tubular portions 42 but also to prevent neighboring medical devices from contacting each other even when elongated medical devices are housed in the tubular portions 42. The tubular portion 42 has a top end opening portion 44 which opens on the side of the basal plate portion 41 and a bottom end opening portion 43 which opens downward, and the top end opening portion 44 and the bottom end opening portion 43 are communicated.

Figure 4A:
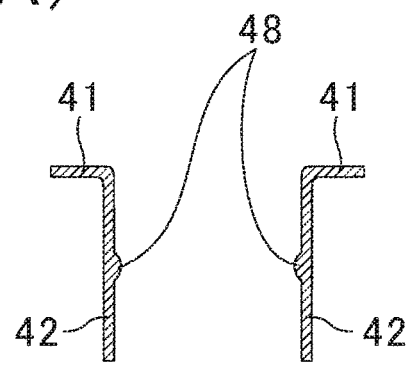
FIG. 4 (A) shows an enlarged cross-section view of a tubular portion of the holder shown in FIG. 1 FIGS. 3(A)
FIG. 4(B) shows an explanatory diagram of a condition where a piston is held in FIG. 4(A).
Figure 4B:
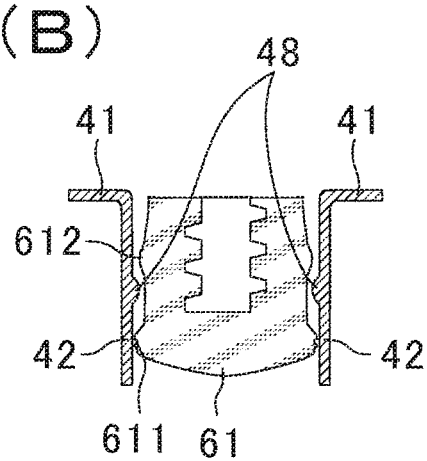

As shown in FIGS. 4(A) and 4(B), a circular convex portion 48 is formed at an upper position from the bottom end by a predetermined length on the inner surface of the tubular portion 42. For example, when a piston 61 as a medical device is housed in the tubular portion 42, the piston 61 is kept in a hanged condition by the circular convex portion 48 to prevent the piston 61 from passing the circular convex portion 48. The circular convex portion 48 may be continuously or intermittently circular. The inner surface of the tubular portion 42 may have a tapered shape which has a diameter decreases upward or downward along the tubular portion 42. The circular convex portion 48 may be formed to make the inner diameter of the portion for a predetermined length from the bottom end (the portion which is lower than the circular convex portion 48) smaller than the inner diameter of the holder 4 at the top end opening portion.

Figure 3C:
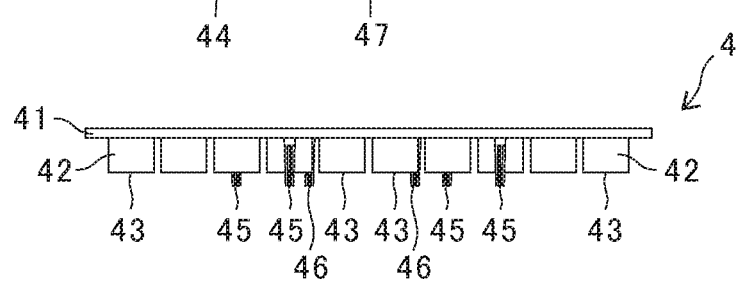

As shown in FIGS. 3(A), 3(B), and 3(C), a side support rod 45 is formed in the peripheral portion of the holder 4 by protruding downward from the basal plate portion 41, and a center support rod 46 is formed in the center portion of the holder 4 by protruding downward from the basal plate portion 41, The side support rod 45 and the center support rod 46 are longer than the tubular portion 42 so that a medical device (not shown in the drawings) housed in the tubular portion 42 contacts neither the bottom surface of the container body 2 nor water on the bottom surface, and does not contact neighboring holders 4 when the holders 4 are stacked.

As shown in FIGS. 5(A)(a), 5(A)(b), 5(B)(a), 5(B)(b), 5(C)(a), 5(C)(b), 5(D)(a), and 5(D)(b), the side support rod 45 comprises a base portion 451 which extends from the basal plate portion 41 by a predetermined length and a connecting support rod portion 452 from the base portion 451 to the tip, and the base portion 451 has a connecting hole 47 forming a recess (a recess for housing the tip of the connecting support rod portion 452 of the side supporting rod 45 of a holder 4 which is positioned above, when multiple holders 4 are stacked) which extends from the side of the basal plate portion 41 toward the side of the connecting support rod portion 452. The base portion 451 may have a circular cylinder shape, an elliptic cylinder shape or a rectangular cylinder.

As shown in the examples of FIGS. 5(A)(a), 5(A)(b), 5(B)(a) and 5(B)(b), the connecting support rod portion 452 may be a rectangular cylinder having a crisscross cross-section shape or a rectangular cylinder having a cross-section shape extending radially in three directions. As shown in the example of FIGS. 5(C)(a) and 5(C)(b), the connecting support rod portion 452 may have a circular cylinder shape from the base portion 451 for a predetermined length and may have a nearly circular cone shape from the end of the circular cylindrical portion to the tip. The connecting support rod portion 452 also may have a circular cone shape from the base portion 451 to the tip. The base portion 451 may be a combination of a rectangular cylinder and a pyramid.

As shown in the example of FIGS. 5(D)(a) and 5(D)(b), the connecting support rod portion 452 has a circular cylinder shape from the base portion 451 for a predetermined length, and has three poles which are thinner than the diameter of the circular cylindrical portion from the circular cylindrical portion to the tip. The connecting support rod portion 452 may be formed by poles from the base portion 451 to the tip, and the number of poles may be one or more. By this arrangement, it is possible to conduct an effective sterilization by coating the entire structure with a sterilization fluid during a sterilization process.

Figure 6B:
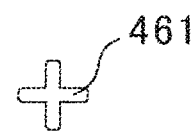
FIGS. 6(*a*) and 6(*b*) show examples of center support rods which are mounted on the holder shown in FIGS. 3(A), 3(B), and 3(C)
Figure 6A:
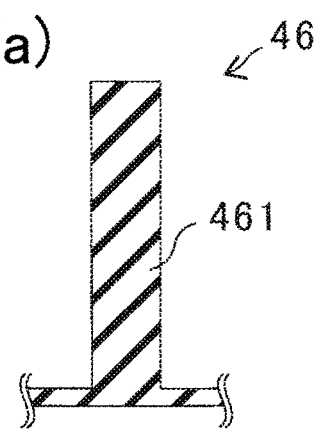

As shown in FIGS. 3(A), 3(B), and 3(C), the center support rods 46 are positioned in the center portion of the holder 4, and the number of the center support rods is two in this example, however it may be one, three or more. The center support rod 46 may have a shape which is same as the shape of the side support rod 45. As shown in the example of FIGS. 6(a) and 6(b), the center support rod 46 may have a shape of a rectangular cylinder having a crisscross cross-section shape from the basal plate portion 41 to the tip, or a rectangular cylinder, a circular cylinder or an elliptic cylinder having a cross-sectional shape extending radially in three directions (when the center support rod 46 has a shape shown in the example of FIGS. 6(a) and 6(b), it is not necessary to form the communicating hole 47).

It is preferable to mold integrally the basal plate portion 41, the tubular portion 42, the side support rod 45 and the center support rod 46. By the integral molding, it is possible to avoid residual bacteria issues in the joint gap between these members.

When the holders 4 are stacked, the tip of the connecting support rod portion 452 of the side support rod 45 of a holder 4 is inserted in the connecting hole 47 on the base end portion of the side support rod 45 of another holder 4 which is already installed (a similar operation is conducted when the center support rod 46 has a structure having a connecting hole 47). By repeating this operation, the stacked arrangement shown in FIG. 7 is obtained. By using such a structure, it is possible to reduce the contact area between the tip surface of the side support rod 45 or the center support rod 46 of the holder 4 and the container bottom portion 21 or the connecting hole 47, and thereby it becomes possible to conduct a sufficient sterilization of the contact portions. It is also possible to conduct an assured sterilization by such a structure of the holder 4 even when the holders 4 are stacked, and thereby it is possible to conduct a sterilization of a large number of medical devices at one time.

Embodiment 2

In a medical device container 1 according to the embodiment 2, the holder 4 in the medical device container 1 according to the embodiment 1 is replaced by a holder 4 shown in FIGS. 8(A) and 8(B) and FIGS. 9(A), 9(B), and 9(C), and the other elements are constituted identical to those in the medical device container 1 according to the embodiment 1.

Figure 8A:
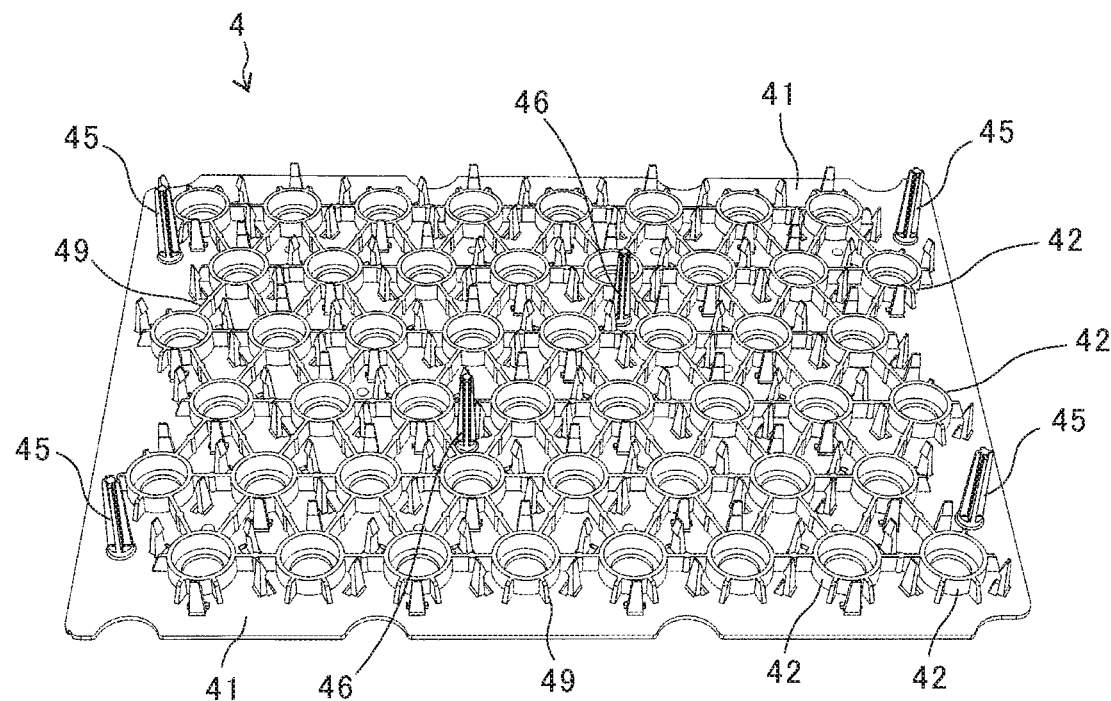
FIG. 8 (A) shows a perspective view (a condition where the bottom turns up) of the embodiment 2 of a holder which is housed in the container for a medical device shown in FIG. 1.
FIG. 8(B) shows a plan view of the holder shown in FIG. 8(A).
Figure 8B:
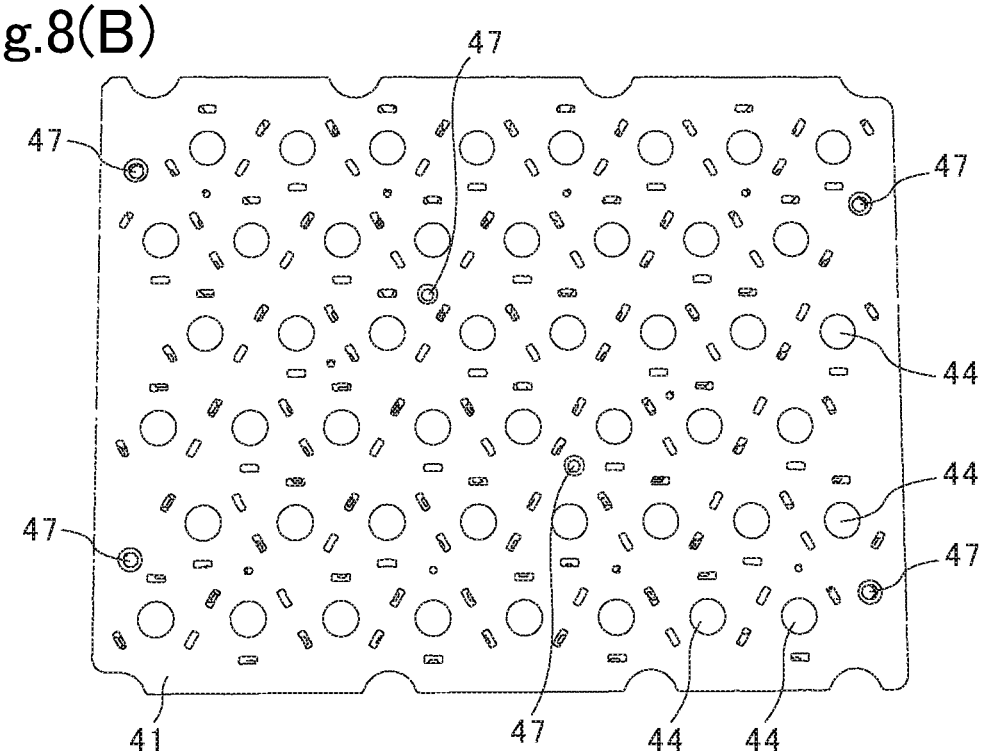
Figure 9A:
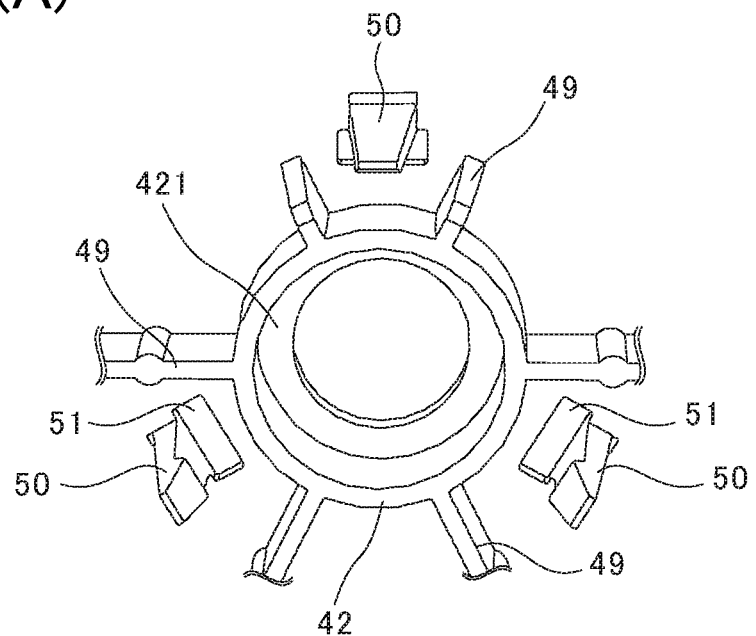
FIG. 9 (A) shows an enlarged perspective view of the holder shown in FIGS. 8(A) and 8(B)
FIG. 9(B) shows an enlarged cross-section view of the holders shown in FIGS. 8(A) and 8(B)
FIG. 9(C) shows a front view of a cap (medical device) which is held by the holder.
Figure 9B:
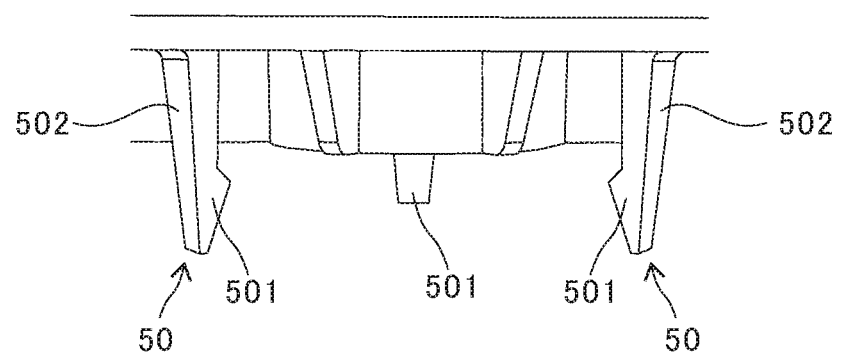

As shown in FIGS. 8(A) and 8(B) and FIGS. 9(A) and 9(B), the medical device holder 4 to be housed in the container body 2 comprises a plate-like basal plate portion 41 and plural tubular portions 42 protruding downward from the basal plate portion 41. In the embodiment 2, as shown in FIG. 8(A) and FIGS. 9(A) and 9(B), plate-like stays 49 are formed to extend from the outside surface of a tubular portion 42 to the outside surface of the neighboring tubular portions 42. A circular flange portion 421 is formed at the base end portion (the side of the basal plate 41) to extend in an inward radial direction from the inner surface of the tubular portion 42.

As shown in FIGS. 9(A) and 9(B), a locking projection 50 protruding downward is formed in the circumference of the tubular portion 42. The locking projection 50 is constituted by a columnar leg portion 502 and a locking claw 501 which protrudes toward the tubular portion 42. In this example, three locking projections 50 are formed in the circumference of each tubular portion 42, however the number of the locking projections 50 is not limited to three and it may be two, four or more. A nearly rectangular pass-through slot 51 is formed between the base end portion of the locking projection 50 and the tubular portion 42. The shape of the pass-through slot 51 is not limited to the shape shown in the drawing, and it may be triangle, oval, circular or polygonal. The position of the pass-through slot 51 is not limited to the area between the base end portion of the locking projection 50 and the tubular portion 42, and it may be a neighborhood of the tubular portion 42. By forming the pass-through slot 51, a sterilization fluid coats the interior portion of the container according the present invention. The other part is identical to that of the holder 4 according to the embodiment 1.

By having the structure of the holder 4 shown in FIGS. 8(A), 8(B), 9(A), 9(B), and 9(C), even when the holders 4 are stacked, it is possible to conduct an assured sterilization and it is possible to sterilize a large number of medical devices at one time.

Figure 9C:
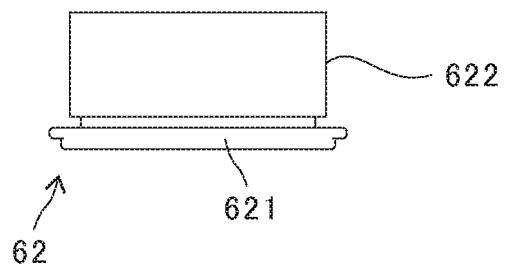

By referring to FIGS. 9(A), 9(B), and 9(C), a way of housing a cap 62 as one example of medical devices in the holder 4 will be explained. A rubber plug (not shown in the drawing) is fitted in the opening portion of a medicine container or the like. The cap 62 is used to cover the rubber plug in order to prevent the rubber plug from desorbing. The cap 62 comprises a top panel 621 and a skirt 622 which protrudes tubularly from the rear side of the top panel 621. The cap 62 is moved the open end of the skirt 622 to face the tubular portion 42, the outer edge of the open end of the skirt 622 contacts the locking claw 501 of the locking projection 50, the locking projection 50 deforms elastically when the cap 62 is further compressed, and then the skirt 622 passes through the locking claw 501. The open end of the cap 62 contacts the circular flange portion 421 of the tubular portion 42, and the open end of the skirt 622 is housed inside of the tubular portion 42. At the same time, the top panel 621 passes the locking claw 501, the locking projection 50 returns elastically, the locking claw 501 covers the upper part of the top panel, and then the cap 62 is housed and kept in the holder 4. The holder 4 is suitable to keep a rubber plug (not shown in the drawing) which is to seal the opening of a medicine container or the like. It is also suitable to keep the cap 62 incorporating a rubber plug.

Embodiment 3

Figure 10:
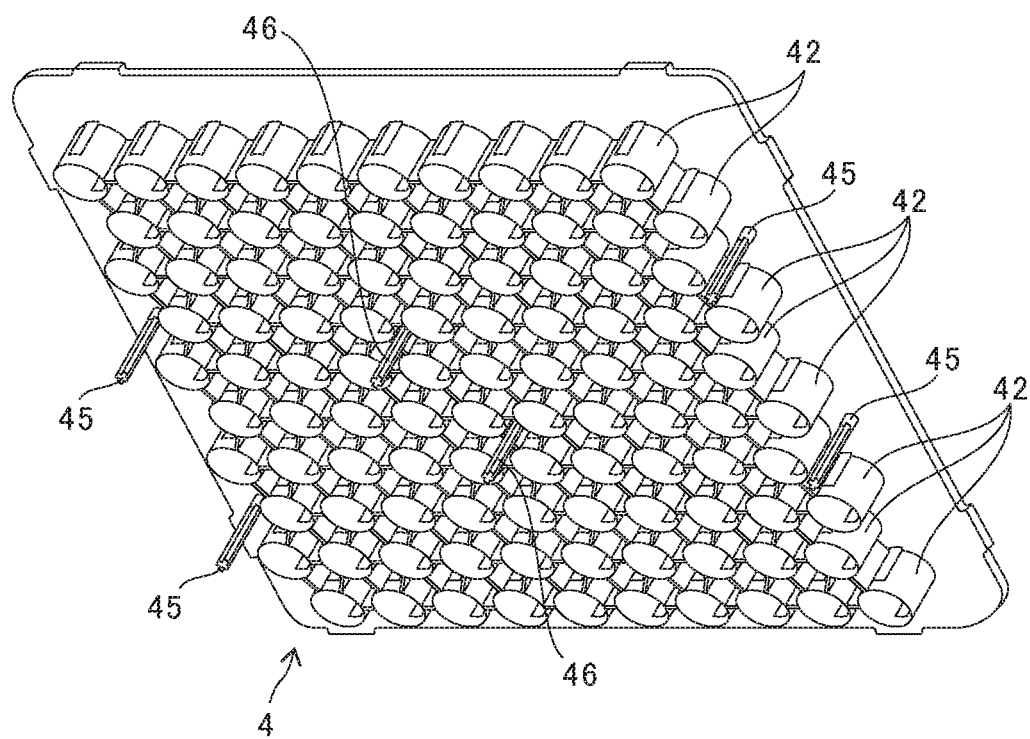
FIG. 10 shows a perspective view of the embodiment 3 of a holder which is housed in the container for a medical device shown in FIG. 1
Figure 11A:
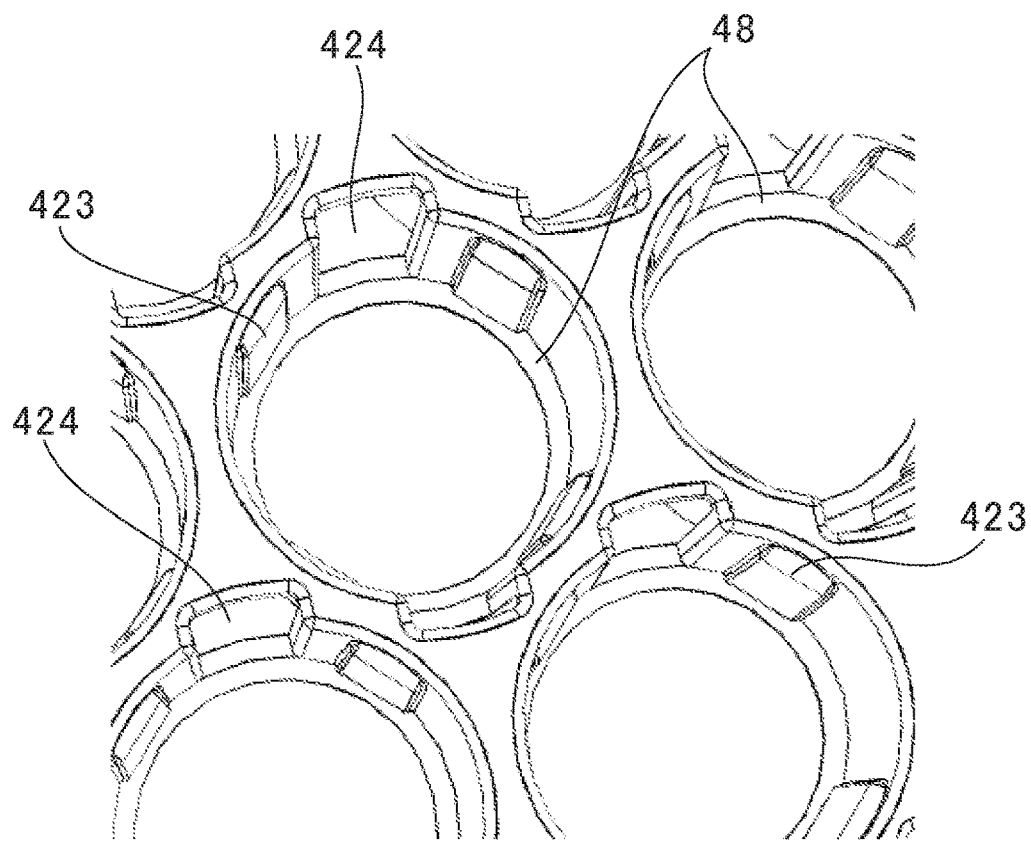
FIG. 11 (A) shows a partial enlarged view of the holder shown in FIG. 10.
FIG. 11(B) shows an enlarged cross-section view of a condition where a vial is held by the holder shown in FIG. 11(A).
Figure 11B:
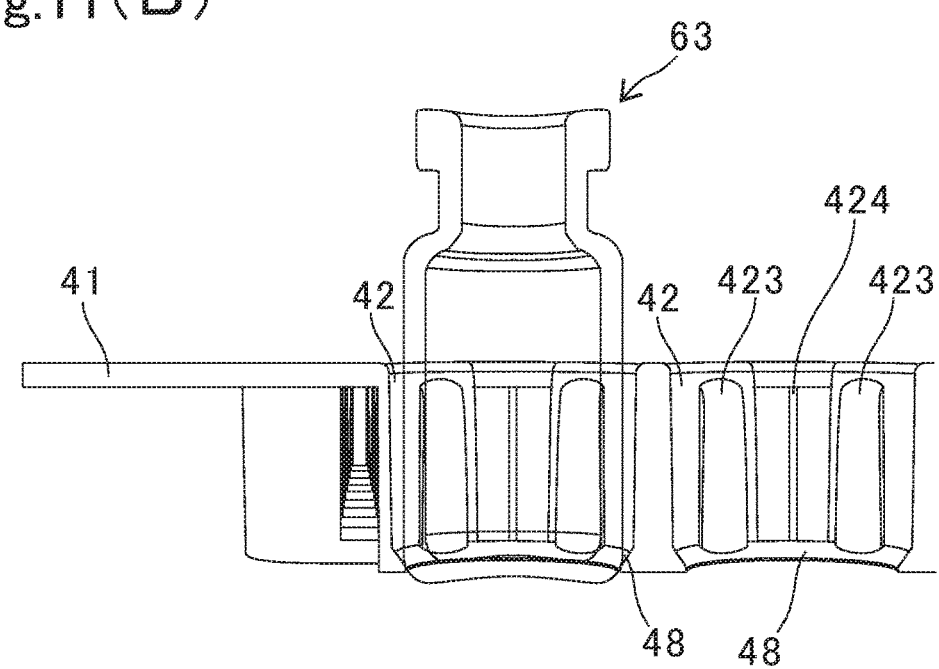

In a medical device container 1 according to the embodiment 3, the holder 4 in the medical device container 1 of the above-mentioned embodiment 1 is replaced by a holder 4 shown in FIG. 10 and FIGS. 11(A) and 11(B), and other elements are identical to those in the medical device container 1 of the embodiment 1.

As shown in FIG. 10 and FIGS. 11(A) and 11(B), a circular convex portion 48 is formed on the inner surface of the lower end portion of the tubular portion 42.

Plural plate-like pads 423 each having a nearly rectangular cross-section shape on the inner surface of the tubular portion 42. Although four pads 423 are positioned at equal spaces in FIGS. 11(A) and 11(B), it is not limited to this arrangement and the number of the pads 423 may be two or more and they may be positioned at unequal spaces. The cross-section shape may be rectangular, circular, oval or polygonal. The shape of the pad 423 is not limited to plate-like, and it may have a predetermined thickness like a dome shape. Plural air holes 424 are formed at the tubular portion 42. The shape of the air hole 424 may be nearly rectangular, circular, oval or polygonal, and it is preferable to make the air hole communicate with the basal plate portion 41. It enables to cover the structure efficiently by a sterilization fluid. Other elements are identical to those of the holder 4 according to the embodiment 1. By having such a structure of the holder 4, even when the holders 4 are stacked, it is possible to conduct an assured sterilization process and it is possible to conduct a sterilization of a large number of medical devices at one time, The holder 4 is especially suitable to hold a medical device like a vial 63. It is possible to prevent the vial 63 from wobbling by the pads 423, and it is also possible to cover the vial 63 with a sterilization fluid by keeping a gap between the vial 63 and the tubular portion 42. The air holes 424 functions to cover the vial 63 efficiently with a sterilization fluid.

A way for housing the vial 63 as one example of a medical device in the holder 4 shown in FIG. 10 and FIGS. 11(A) and 11(B) will be explained. The vial 63 is housed and kept in the holder 4 by inserting the bottom of the vial 63 in the opening portion (the side of the basal plate portion 41) which is positioned above the tubular portion 42, contacting the circumferential portion of the bottom surface of the vial 63 with the circular convex portion 48 and contacting the side surface of the vial 63 with the pad 423.

Embodiment 4

Figure 12A:
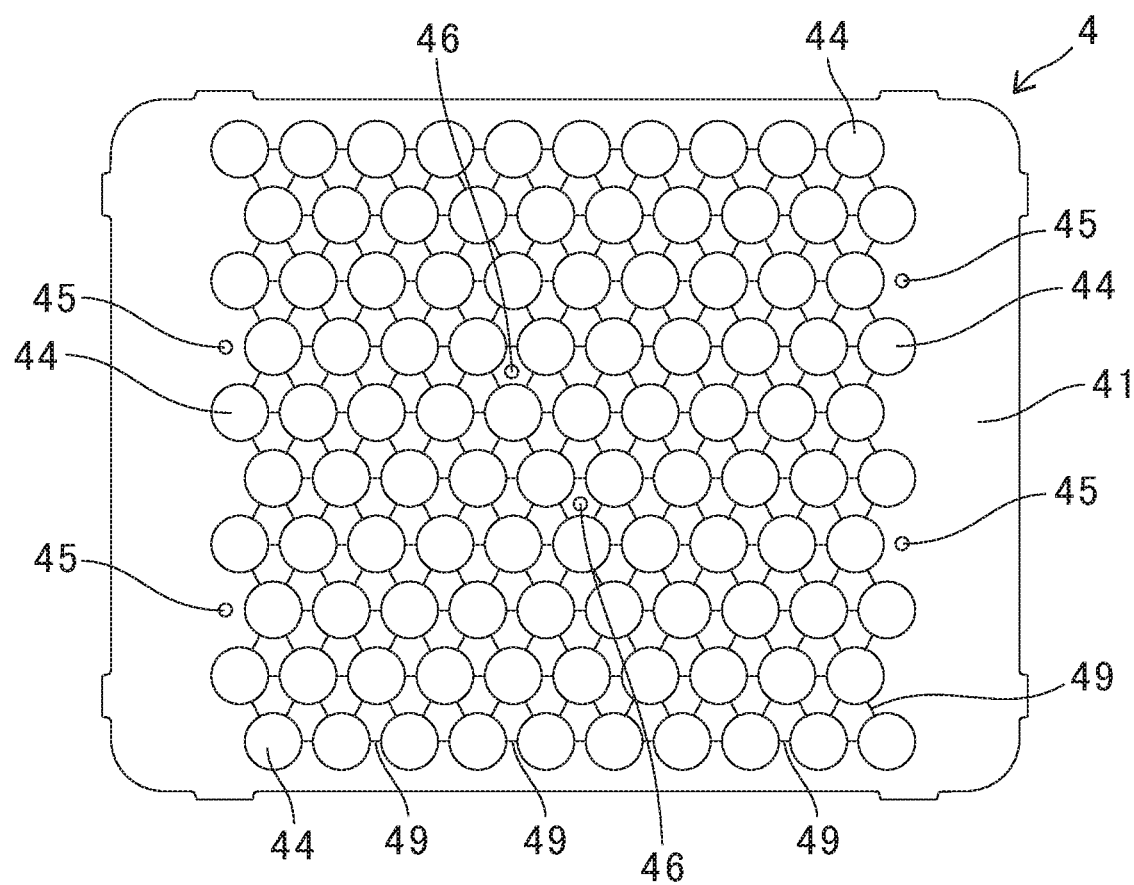
FIG. 12 (A) shows a plan view of the embodiment 4 of a holder which is housed in the container for a medical device shown in FIG. 1.
FIG. 12(B) shows a front view of the holder shown in FIG. 12(A).
Figure 12B:
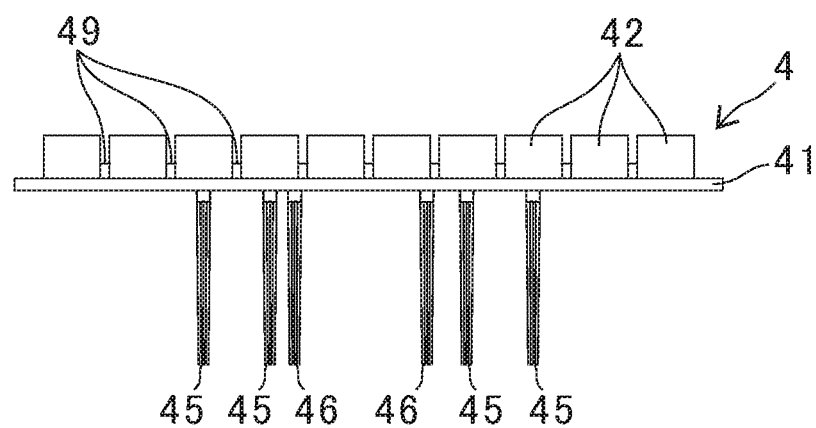
Figure 14:
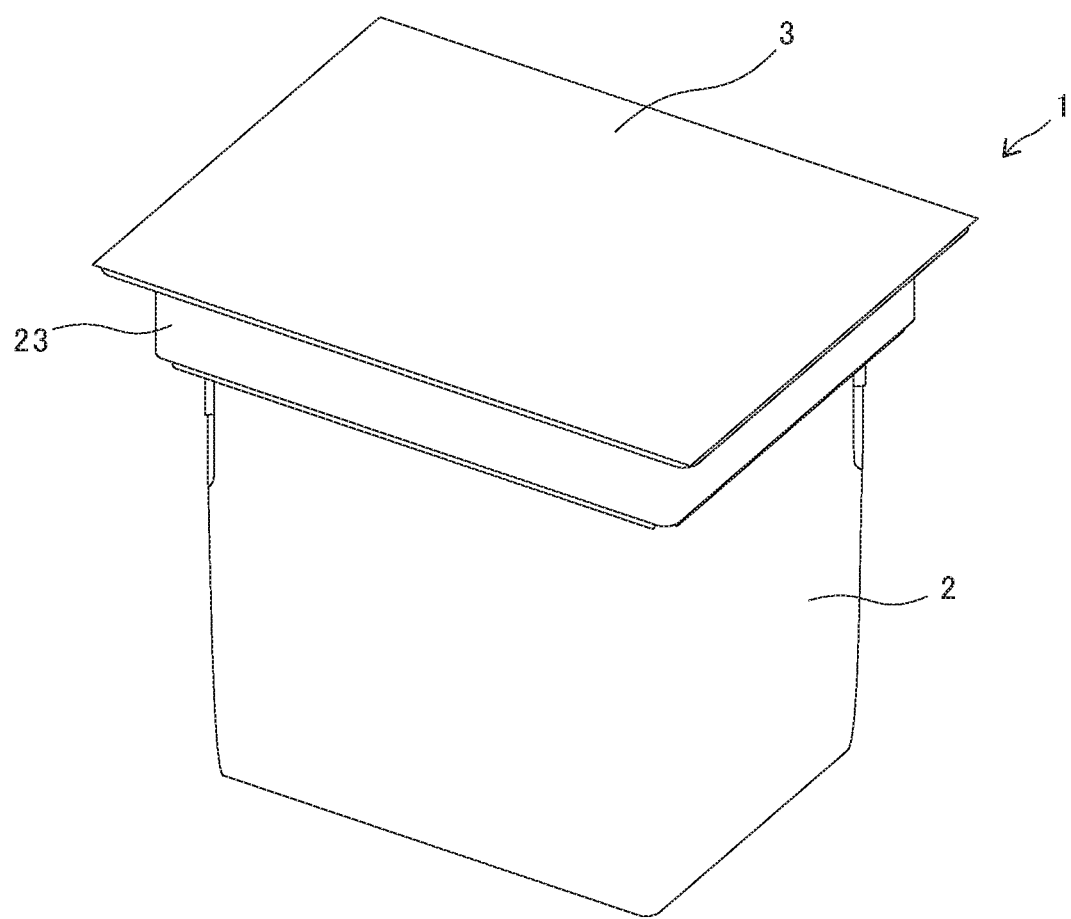
FIG. 14 shows a perspective view of the embodiment 4 of the container for a medical device according to the present invention.

In a medical device container 1 according to the embodiment 4, the holder 4 in the medical device container 1 according to the above-mentioned embodiment 1 is replaced by a holder 4 shown in FIGS. 12(A) and 12(B), the container body 2 shown in FIG. 1 and FIGS. 2(A) and 2(B) is replaced by a container 2 shown in FIG. 14, and other elements are identical to those in the medical device container 1 according to the embodiment 1.

Figure 13:
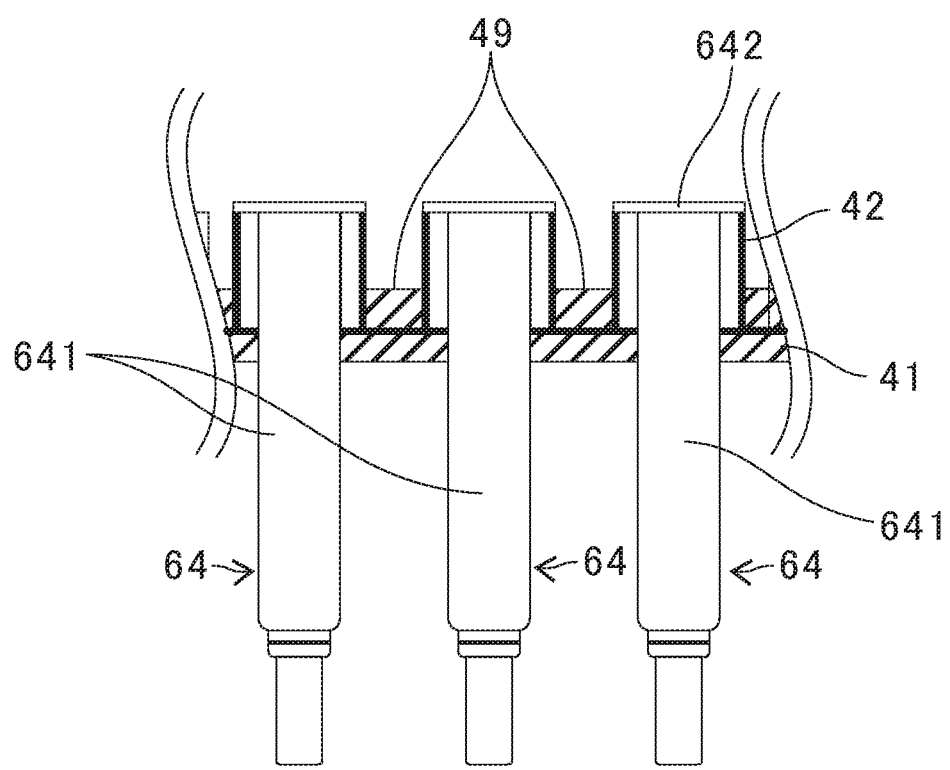
FIG. 13 shows an enlarged cross-section view of a condition where a syringe is held by the holders shown in FIGS. 12(A) and 12(B).

As shown in FIGS. 12(A) and 12(B) and FIG. 13, the medical device holder 4 to be housed in the container body 2 comprises a plate-like basal plate portion 41 and plural tubular portions 42 protruding upward from the basal plate portion 41. A plate-like stay 49 is positioned between the neighboring tubular portions 42. A side support rod 45 and a center support rod 46 are longer than those in the embodiment 1. In this embodiment, they are constituted to house a medical device like a syringe 64.

As shown in FIG. 14, the container body 2 has a geometry which is deeper (higher) than that in the embodiment 1. In this embodiment, the container body 2 is constituted to house an elongated medical device like a syringe 64. Other structures are identical to those of the holder 4 in the embodiment 1. By having such a configuration of the holder 4, even when the holders 4 are stacked, it is possible to conduct an assured sterilization process and it is also possible to conduct a sterilization of a large number of medical devices at one time.

A way of housing the syringe 64 as one example of medical devices in the holder 4 shown in FIGS. 12(A) through 14 will be explained. The syringe 64 comprises a nearly tubular syringe body 641 and a flange 642 formed at the base end portion. The flange 642 is a torus-shape disk portion formed to extend in a radial direction from the entire back-end periphery of the syringe body 641. When the tip of the syringe 64 is inserted into the upper opening portion of the tubular portion 42, the torus-shape disk portion of the flange 642 of the syringe 64 contacts with the top end of the tubular portion 42, and the syringe 64 is kept being hung.

As described above, each holder 4 shown in the embodiments 1 through 4 can be stacked by using holders 4 having not only a same shape but also optionally selected different shapes. For example, the holder 4 shown in the embodiment 2 (FIGS. 8(A) and 8(B)) may be stacked above the holder 4 shown in the embodiment 1 (FIGS. 3(A), 3(B), and 3(C)), and the holder 4 shown in the embodiment 3 (FIG. 10) may be stacked above the holder 4 shown in the embodiment 2.

The container 1 according to the present invention may house not only a same type of medical devices like pistons only or vials only but also a combination of different types of medical devices like a combination of vials and caps or a combination of syringes and pistons.

The medical device container 1 according to the present invention can be produced as described below, however the process is not limited to the following. First, medical devices are placed in a holder 4, the holder 4 is housed in a container body 2, the opening portion of the container body 2 is sealed by a sterilizable film, and it is sterilized in a sterilization equipment. Then, under a clean environment, the sterilizable film is covered and sealed by a sterilized gas non-permeable film 3. The medical device container 1 produced in this way is delivered to pharmaceutical companies or medical institutions after sterilizing the outside surface of the medical device container 1 in a sterilization equipment and then packaging it.

EXPLANATION OF REFERENCES 1 medical device container
2 container body
21 container bottom portion
22 circular flange portion
23 uneven portion
3 gas non-permeable film
4 holder
41 basal plate portion
42 tubular portion
421 circular flange portion of tubular portion
423 pad
424 air hole
43 bottom end opening portion
44 top end opening portion
45 side support rod
451 base portion
452 connecting support rod portion
46 center support rod
47 connecting hole
48 circular convex portion
49 stay
50 locking projection
501 locking claw
502 leg portion
51 pass-through slot
61 piston
62 cap
621 top plate
622 skirt
623 rubber plug
63 vial
64 syringe
641 syringe body
642 flange

The invention claimed is:

1. A container, comprising
an upper opening portion;
a holder and anther holder stacked on the holder, which are placed in the container, each of the holder and the another holder including
a basal plate portion having a plate shape,
a plurality of tubular portions protruding downwardly from the basal plate portion,
a convex portion protruding inwardly from an inner surface of each of the plurality of tubular portions adapted to hold a medical device, and
a support rod protruding downwardly from the basal plate portion and having a length longer than the plurality of tubular portions, the support rod including a base portion extending from the basal plate portion, a connecting support rod portion extending from the base portion to a tip of the connecting support rod portion, and a connecting hole forming a recess from the basal plate portion toward the connecting support rod portion; and
a gas non-permeable film for sealing the opening portion,
wherein the connecting support rod portion of the another holder has a rectangular cylinder portion having a crisscross shape in a cross-section thereof, and the another holder is arranged such that the tip of the connecting support rod portion of the another holder is inserted in the connection hole of the holder on the base end portion of the support rod of the holder to conduct an effective sterilization, and
each of the holder and the another holder further includes another supporting rod having a length longer than the plurality of tubular portions, and the supporting rod of each of the holder and the another holder is arranged at a center portion thereof and the another supporting rod of each of the holder and the another holder is arranged at a side portion thereof.

2. A container according to claim 1, wherein the gas non-permeable film includes a sterilizable film which is sterilizable by gas, steam or radial ray, and the sterilizable film is positioned on a side of contacting the container.

* * * * *

UNITED STATES PATENT AND TRADEMARK OFFICE
CERTIFICATE OF CORRECTION

Page 1 of 1

PATENT NO. : 10,874,473 B2
APPLICATION NO. : 16/095812
DATED : December 29, 2020
INVENTOR(S) : Hiroshi Togashi et al.

It is certified that error appears in the above-identified patent and that said Letters Patent is hereby corrected as shown below:

In the Specification

Please add the following after the "." in Column 4, Line 65:
--FIG. 4(B) shows a condition where the piston 61 is inserted from the top end opening portion of the tubular portion 42, a first rib (formed at a position nearer to the tip) 611 passes the circular convex portion 48, a second rib 612 does not pass the circular convex portion 48 and is held at the circular convex portion 48, and the piston 61 is kept hanging.--.

Signed and Sealed this
Twenty-seventh Day of April, 2021

Drew Hirshfeld
*Performing the Functions and Duties of the
Under Secretary of Commerce for Intellectual Property and
Director of the United States Patent and Trademark Office*